US012649831B2

(12) United States Patent
Min et al.

(10) Patent No.: US 12,649,831 B2
(45) Date of Patent: Jun. 9, 2026

(54) PLASTICISED SUPERPOROUS HYDROGEL

(71) Applicant: Oxford Medical Products Limited, Witney (GB)

(72) Inventors: Xue Min, Witney (GB); Anthony John Fitzpatrick, Witney (GB); Jan Tadeusz Czernuszka, Witney (GB); Camilla Easter, Witney (GB)

(73) Assignee: Oxford Medical Products Limited, Witney (GB)

( * ) Notice: Subject to any disclaimer, the term of this patent is extended or adjusted under 35 U.S.C. 154(b) by 952 days.

(21) Appl. No.: 17/768,057

(22) PCT Filed: Oct. 12, 2020

(86) PCT No.: PCT/EP2020/078654
§ 371 (c)(1),
(2) Date: Apr. 11, 2022

(87) PCT Pub. No.: WO2021/069751
PCT Pub. Date: Apr. 15, 2021

(65) Prior Publication Data
US 2024/0092977 A1 Mar. 21, 2024

(30) Foreign Application Priority Data
Oct. 11, 2019 (GB) ..................................... 1914779

(51) Int. Cl.
C08J 3/075 (2006.01)
A61K 9/00 (2006.01)
A61K 47/34 (2017.01)
C08J 3/24 (2006.01)

(52) U.S. Cl.
CPC ............. *C08J 3/075* (2013.01); *A61K 9/0056* (2013.01); *A61K 47/34* (2013.01); *C08J 3/246* (2013.01)

(58) Field of Classification Search
None
See application file for complete search history.

(56) References Cited

U.S. PATENT DOCUMENTS

| 2004/0059370 A1 | 3/2004 | Greene, Jr. et al. |
| 2006/0100664 A1 | 5/2006 | Pai et al. |
| 2014/0353248 A1 | 12/2014 | Oka et al. |
| 2018/0168563 A1 | 6/2018 | Mylonakis et al. |
| 2021/0038871 A1 | 2/2021 | Zhao et al. |

FOREIGN PATENT DOCUMENTS

| CN | 1488331 A | 4/2004 |
| CN | 108722196 A | 11/2018 |
| WO | 98/51408 A1 | 11/1998 |
| WO | 2013099968 A1 | 7/2013 |
| WO | 2014032189 A1 | 3/2014 |
| WO | 2019/016560 A1 | 1/2019 |
| WO | 2019/152183 A1 | 8/2019 |

OTHER PUBLICATIONS

Fisher Scientific "Simulated Gastric Fluid (without Pepsin)" <https://www.fishersci.com/shop/products/simulated-gastric-fluid-without-pepsin-ricca-chemical/710816> accessed Aug. 1, 2025 (Year: 2025).*
Office Action issued on Dec. 28, 2023, in Chinese Patent Application No. 202080023529.9.
Combined Search & Examination Report issued for Application No. GB1914779.2, dated Apr. 30, 2020, 7 pages.
Search Report issued for Application No. GB1914779.2, dated Jul. 31, 2020, 4 pages.
International Search report and Written Opinion issued for Application No. PCT/EP2020/078654, dated Jan. 21, 2021, 16 pages.
Omidian, Hossein, Jose G. Rocca, and Kinam Park. "Elastic, superporous hydrogel hybrids of polyacrylamide and sodium alginate." Macromolecular bioscience 6.9 (2006): 703-710.
Xinyue Liu et al., "Ingestible hydrogel device", Nature Communications vol. 10, 493 (2019), 10 pages.
Third Office Action issued in Chinese Patent Application No. 202080023529.9.
Second Office Action issued on Oct. 22, 2024, in Chinese Patent Application No. 202080023529.9.
Second Examination Report issued on Feb. 1, 2023, in Saudi Arabian Patent Application No. 522432217.
First Office Action issued on Apr. 26, 2024, in Chilean Patent Application No. 202200611 and English summary.
Search Report issued on Apr. 26, 2024, in Chilean Patent Application No. 202200611.
Second Office Action issued on Nov. 5, 2024, in Chilean Patent Application No. 202200611 and English summary.
Search Report issued on Nov. 5, 2024, in Chilean Patent Application No. 202200611.
International Preliminary Report on Patentability in connection to PCT/EP2020/078654, dated Apr. 12, 2022. 8 pages.
Examination Report issued on Mar. 11, 2024, in Kuwait Patent Application No. KW/P/2022/000295.
Search Report issued on Dec. 4, 2023, in Brazilian Patent Application No. 112022004836.0.
Office Action issued on Sep. 18, 2024, in Japanese Patent Application No. 2022-521632.

(Continued)

*Primary Examiner* — Nicole P Babson
(74) *Attorney, Agent, or Firm* — Meunier Carlin & Curfman LLC

(57) ABSTRACT

The invention provides a process for preparing a plasticised superporous hydrogel material comprising subjecting initial hydrogel material to treatment with an acidic solution, an optional treatment with a monovalent metal salt solution, freeze drying and plasticisation. Optionally, the process of the invention produces moulded plasticised superporous hydrogel material bodies that have one or more through-holes formed therein. The plasticised superporous hydrogel material of the present invention may be formulated as a suitable oral dosage form for use an appetite suppressant and for use to deliver a pharmaceutical and/or nutraceutical into a human or animal body.

14 Claims, 8 Drawing Sheets

(56)           References Cited

OTHER PUBLICATIONS

Examination Report mailed on Dec. 3, 2025, in European Application No. 20793291.4.

Examination Report mailed on Oct. 15, 2025, in Australian Application No. 2020365048.

\* cited by examiner

26

28

30

38a    40a    30    40b    38b

36

38a    42    38b

44

PLASTICISED SUPERPOROUS HYDROGEL

CROSS REFERENCE TO RELATED APPLICATIONS

This application is a United States National Phase Patent Application of International Patent Application Number PCT/EP2020/078654, filed on Oct. 12, 2020, which claims the benefit of priority to GB Application No. 1914779.2, filed Oct. 11, 2019, contents of which are incorporated by reference herein in their entireties.

FIELD OF THE INVENTION

The present invention relates to a process for the preparation of hydrogel materials which can be more easily and more reliably manipulated, and which have an increased swelling volume and an increased rate of swelling compared with known hydrogel materials. The hydrogel materials produced by the process of the present invention are particularly suitable for use as, or in, oral dosage capsules, for example as appetite suppressants for both humans and animals. Additionally, the hydrogel materials produced by the process of the present invention, both when used per se (as made) and when used in the form of a suitable dosage formulation, may comprise, incorporate or encapsulate one or more pharmaceuticals, nutraceuticals or foreign bodies to be eluted or otherwise delivered, within the human or animal body, or into any liquid (preferably aqueous) media-based application in general.

BACKGROUND OF THE INVENTION

As discussed in "Recent developments in superporous hydrogels" by H. Omidian et al in J. Pharm. & Pharmacol. 2007, 59:317-327, superporous hydrogels (SPH) are porous hydrophilic cross-linked structures which are hard and brittle when dried, and insoluble in water. However, when immersed in aqueous media, they can absorb the aqueous fluids up to many times their own weight, to swell in size and to become soft yielding gel materials. SPHs typically have a three-dimensional network made from hydrophilic polymeric material, with numerous pores with an average size larger than 100 µm up to around 1 or 2 mm. It is these pores, by being connected together to form open channel structures, which use capillary action to absorb water very rapidly. Maximum swelling is generally reached in a fraction of a minute and the SPH swells to an equilibrium size.

Recently published patent application WO2019016560 (A1), describes a process to soften (plasticise or render malleable) the dried superporous hydrogel materials without the need for them to swell. The process further describes forming a sheet of plasticised superporous hydrogel material by applying a compressive force to flatten/collapse the hydrogel pores without breaking the bonds that hold the three-dimensional network structure together. Oral dosage formulations may be produced by cutting samples from the sheet of superporous hydrogel material, folding/rolling these samples and then inserting them into a casing for an oral dosage capsule.

Such oral dosage formulations will dissolve or rupture on contact with an aqueous medium (for example the gastric fluids when the capsule is swallowed by a human or animal), and the superporous hydrogel contained inside will then rapidly swell many times its original size. These formulations are disclosed to make excellent appetite suppressants and useful alternatives to a gastric balloon in the treatment of obesity.

The present invention seeks to provide a quick, cost effective and reliable process for making superporous hydrogel materials which have excellent physical characteristics (including swelling volume, rate of swelling, and overall strength) and which, importantly, are able to be easily manipulated, for example to assist in their direct moulding or their insertion into a casing of an oral dosage formulation. The aim of the process of the present invention is to avoid the need to form a sheet of plasticised superporous hydrogel (for example by the application of a high compressive force to the as made of plasticised superporous hydrogel material), and to avoid the need to cut samples of hydrogel from the sheet and then to roll these prior to insertion into an oral dosage capsule casing. Ideally therefore, the superporous hydrogels made by the process of the present invention will be able to be cast into a mould and then manipulated directly, for example into an oral dosage capsule casing (shell). Alternatively, the superporous hydrogel made by the process of the present invention will be able to be cast or compressed directly into a lozenge shaped dosage formulation for direct oral administration.

The present invention further provides superporous hydrogel materials which, once swallowed and swollen, will on the one hand have a mechanical robustness that makes products made therefrom able to be retained for a limited period of time, for example 1 to 4 weeks, without degradation and/or digestion, in the stomach of a human or animal, and therefore able to be used in appetite suppressant and appetite control applications in overweight/obese animal or human patients or as a delivery vehicle for a controlled release of pharmaceutical or nutraceutical within the animal or human body, and which on the other hand will start to breakdown or disintegrate naturally over time, for example after 1 to 4 weeks, and be excreted naturally out of the body. A suitable appetite suppressant will ideally be a tablet or other suitable oral dosage format which is designed to be taken at home and without the need for a hospital or health care setting. Further ideally, the appetite suppressant of the present invention will not require surgery, endoscopy or radiation to insert, fit, or check correct the placement of the appetite suppressant formulation within the patient's body. Advantageously, such an appetite suppressant formulation will be effective for several days or several weeks at a time, before termination is triggered by automatic degradation or by the consumption of approved chemical or natural food sources, followed by excretion. Further advantageously, the aim of the present invention is to provide appetite suppressants which will also allow patients to be able to ingest more or fewer doses of the one or more superporous hydrogels and also to terminate the effects of ingested appetite suppressant product at will. Consequently, the present invention also provides methods for breaking down the appetite suppressant formulations of the present invention once ingested by the patient and provides appetite suppressant products that are customised according to the required strength and duration of the weight control process.

In a further object, the present invention provides plasticised superporous hydrogel materials for use in an oral dosage formulation (e.g. a dosage capsule) which may additionally comprise one or more pharmaceuticals and/or nutraceuticals which will be designed to be eluted or otherwise delivered into the human or animal body, for example once the capsule is in a specific location in the body (for example in the stomach or the intestine). Ideally, the pharmaceutical/nutraceutical will be eluted/delivered over an extended period of time. In one embodiment, it is envisaged that the one or more pharmaceuticals and/or nutraceuticals are incorporated within an oral dosage formulation as an additional separate ingredient to the plasticised hydrogel material. In this embodiment, the pharmaceutical and/or nutraceutical may be used alone, or in combination with one or more additives. Alternatively, the pharmaceutical and/or nutraceutical may be associated with, or be contained within, a separate drug delivery device, such as liposomes. In another further embodiment, the pharmaceutical and/or nutraceutical may be part of the structure of the hydrogel material, for example the pharmaceutical and/or nutraceutical may be attached to one or more of the hydrophilic polymer chains which form the hydrogel material. As used herein, the term "nutraceutical" is to be interpreted to include any food supplement, mineral or vitamin which gives health enhancing benefits when ingested by a human or animal.

In a preferred embodiment, the present invention provides a process for preparing a plasticised superporous hydrogel material comprising the steps:

a) forming an initial hydrogel material without the use of a blowing agent or other foaming means, wherein the initial hydrogel material comprises one or more selected from an interpenetrating network structure, a semi-interpenetrating network structure and a simple cross-linked structure formed by providing a mixture comprising one or more hydrophilic polymers and/or copolymers and subjecting the mixture to polymerisation and/or cross-linking conditions;

b) recovering the resulting the initial hydrogel material formed in step a) and treating it with an acidic solution comprising one or more acids, and with a pH in the range <1 to ≤3;

c) treating the initial hydrogel material formed in step a), either concurrently with, or after, treatment step b), with a ≥0M to ≤1.5M solution comprising one or more monovalent metal salts;

d) drying the resulting wet initial hydrogel material using freeze drying, to produce a dried superporous hydrogel material;

e) treating the resulting dried superporous hydrogel material to plasticise its structure; and f) recovering the resulting plasticised superporous hydrogel material.

It is known to use a blowing agent or other foaming means during prior art polymerisation/copolymerisation and cross-linking processes. Although this produces a "superporous" hydrogel, the present Applicant has found that the efficiency of the process, as well as the quality of the final superporous hydrogel, are compromised. Firstly, the use of a blowing agent or other foaming means during the polymerisation step will require the superporous hydrogel product material to be separated from the polymer reaction mixture and then dried. The normal way to achieve drying is to air or oven dry, however, as explained below, we have found that such a process is too slow to ensure that all of the solvent (typically water) is removed sufficiently quickly to prevent the pores collapsing. Secondly, pore size is determined by the size of the bubbles of gas either generated by the blowing agent or as provided by the foaming means and as it is difficult to manage the size of these gas bubbles, it is consequently difficult to control the size of the pores. Thirdly, the use of a blowing agent or other foaming agent and the subsequent separation/drying of the resulting superporous hydrogel constitutes two steps whereas the present invention only requires a single freeze-drying step to accomplish both superporosity and drying. Finally, fourthly, the use of a blowing agent generally uses a sodium carbonate or sodium hydrogen carbonate to general carbon dioxide as the pore forming gas, however, this requires the polymerisation step to be conducted under acid conditions. This may be convenient for systems which make acrylic acid-based polymers however, it is not so when an acrylamide-based or an amide-based polymer is used.

The ideal initial hydrogel used in the process of the present invention is a "co-hydrogel", that is, a hydrogel which comprises two or more crosslinked interpenetrating backbones that are formed from one or more hydrophilic polymers and/or copolymers. The rate of swelling and rate of subsequent breakdown of the resulting plasticised superporous hydrogel material are advantageously much easier to control when the hydrogel comprises two or more crosslinked interpenetrating backbones compared with a hydrogel made using a single crosslinked backbone.

The hydrophilic polymers and/or copolymers may be derived from naturally occurring polymers and monomers, from synthetic polymers and monomers, or from mixtures of naturally occurring and synthetic polymers and monomers. Preferably, the one or more hydrophilic polymers are hydroxylated polymers, and further preferably, the hydrophilic polymers are selected from $C_1$-$C_6$-alkylcelluloses, hydroxy-$C_1$-$C_6$-alkylcelluloses, hydroxy-$C_1$-$C_6$-alkyl-$C_1$-$C_6$-alkyl-celluloses. Further preferably, the one or more hydrophilic polymers are selected from methylcellulose, ethylcellulose, n-propylcellulose, hydroxyethylcellulose, hydroxy-n-propylcellulose, hydroxy-n-butylcellulose, hydroxypropylmethylcellulose, ethylhydroxyethylcellulose, carboxymethylcellulose, carboxymethylstarch, chitosan, alginate, cationic dextran, (e,g, dextran sulfate, dextran phosphate, dimethyl aminodextran, diethyl aminodextran, cationic dextrin, polyetherimide, heparin, hyaluronic acid, chondroitin, chondroitin sulfate, heparan sulfate, polygalacturonic acid, polyanuronic acid, polygalacturonic acid polyarabinic acid and polylysine. In some cases, the one or more hydrophilic polymers may be made by the polymerisation and/or copolymerisation of one or more monomers selected from $C_1$-$C_6$-alkenyl amides (e.g. to make polyacrylamide) and $C_1$-$C_6$-alkenyl acids (e.g. to make acrylic acid). Other possible preferred polymers include poly(acrylamide), poly(2-acrylamido-2-methyl-1-propanesulfonic acid) and poly(N-isoacrylamide).

It is particularly advantageous that the one or more hydrophilic polymers and/or copolymers used in the process of the present invention are at least in part derived from an amine monomer and/or an acrylamide monomer and/or an amine-moiety containing monomer and/or an acrylamide moiety-containing monomer, optionally together with a polymer that comprises multiple OH-groups and/or a multi OH-group containing monomer. Suitable multi-OH group containing materials include alginate, chitosan, and other sugar or carbohydrate-containing materials. It is advantageous that the cross-linking agent comprises calcium. It is preferred that the one or more hydrophilic polymers are not derived from acrylic acid monomer or acrylic acid moiety-containing monomer.

An initial hydrogel is preferably prepared using one or more hydrophilic polymers and/or one or more monomers, as described above, optionally in combination with one or more further components selected from biocompatible polymers and mechanically strong hydrogels.

Suitable biocompatible polymers include one or more selected from: polyallyl alcohol, polyvinyl alcohol, poly-acrylic acid, polyethylene glycol and poly(N-vinyl-2-pyr-rolidone) (PVP), and these may be copolymerised with one or more further polymers, for example, acrolein.

Ideally, the one or more hydrophilic polymers (as discussed above), from which the initial hydrogel is made, will either be chosen to impart suitable mechanical properties or toughness to the final product, or alternatively suitable mechanically strong hydrogels can be added either to the initial hydrogel once formed, or to a mixture of the one or more monomers used to prepare the initial hydrogel. Such strong materials include non-superporous and slow-swelling hydrogels, also known as superabsorbent polymers (SAP) which are hydrophilic networks that can absorb and retain huge amounts of water or aqueous solutions. Preferably, they can uptake water as high as 100,000%. Further preferably, the one or more mechanically strong slow swelling non-superporous hydrogels are selected from double network hydrogels (DN), nanocomposites hydrogels (NC), topological hydrogels (TP), macromolecular composite hydrogels (MMC). Particularly useful slow swelling non-superporous hydrogels include, but are not limited to, poly (2-acrylamido, 2-methyl, 1-propanesulfonic acid) (PAMPS)-polyacrylamide (PAAm) double network hydrogel, Argarose-Hydroxyethyl Methacrylate (HEMA) double network hydrogel, Alginate-PAAm double network hydrogel, poly (N-isopropyl acrylamide) and poly(N-isopropyl acrylamide)-laponite nanocomposite hydrogel. Although such slow swelling non-superporous hydrogels have a limited swelling rate, they may nevertheless have a reasonable swelling capacity of up to 15-20 folds in terms of volume increase from xerogel to fully swollen state. When reaching their swollen equilibrium, the non-superporus hydrogels can still retain a maximum engineering compression strength of 2-3MPa or larger, however, generally with limited volume swelling ratio. Suitable non-superporous hydrogels may exhibit a high overall swelling capacity but a slower rate of swelling than the high-volume swelling superporous hydrogels of the present invention.

Samples of the initial hydrogel material are preferably made by a cast moulding process which may involve filling a suitably shaped and sized mould with a mixture of the polymers and/or monomers such as described above (together with one or more optional further components as discussed above) and subjecting the mixture to the addition of one or more cross-linking agents, and/or to irradiation (for example with a high-energy ionizing radiation such as electron beam (e-beam), gamma or x-ray radiation), and/or other conditions suitable for generating a crosslinked polymerised and/or copolymerised, interpenetrating network, or the semi-interpenetrating network or the simple cross-linked structure of the hydrogel (such as sulfur vulcanisation or other suitable chemicals, optionally in conjunction with heating and/or increased pressure). It is important to control the degree of cross-linking, however, so that it does not interfere with the swelling volume ratio of the product. Ideally, the demoulded initial porous hydrogel is in individual pieces with typical dimensions being in the range 15 mm×25 mm to 40 mm×60 mm. The individual pieces (samples or bodies) of initial porous hydrogel will be of any suitable shape and or size, and preferably will be cube-, cuboid-, ovoid-, pellet-, bead-, ball-, cylinder-, rod-, or irregularly- shaped bodies. In an alternative process, the initial hydrogel material will be moulded or extruded into, for example, a long cylinder or tube of pre-designed diameter and then cut into required lengths after curing (cross-linking).

Individually moulded or cut extruded samples initial hydrogel material preferably have an inner body portion (which may be solid or hollow) and an outer surface which is the exterior boundary of the inner body portion that is formed against the inside of the mould or extrusion die.

Alternatively, the samples of initial hydrogel material may be non-moulded but will also preferably have an inner body portion with an internal structure comprising plasticised superporous hydrogel material, and an outer surface which is the exterior boundary of the inner body portion.

The processing steps described hereafter will be equally be applicable to non-moulded, and moulded (including cast moulded and non-cast moulded) (e.g. as made, or in sheet form or extruded or otherwise compressed) initial hydrogel material.

Once prepared, the initial hydrogel material is preferably washed with a suitable solvent (ideally distilled water) to remove any unreacted hydrophilic polymers and/or monomers from the initial hydrogel. The initial hydrogel material is then treated with at least one acidic material (preferably by being submerged in an acidic solution) for up to 14 days, preferably 7 to 14 days, and further preferably then subjected to a daily routine of being flushed with water (ideally distilled water) and re-treating with fresh acidic material or, preferably, re-submerging in fresh acidic solution. Typically, the volume of acidic solution used to soak the initial hydrogel samples is 15 to 50 ml per initial hydrogel sample, and this will cause the sample of initial hydrogel material to swell. As described below in the specific examples, acid treatment beneficially i) improves the rate of swelling of the target plasticised superporous hydrogel material, ii) allows control of the % change in swelling volume, iii) allows control of the degree of porosity in the target superporous hydrogel and iv) allows control over the degree of malleability (also referred to herein as "ease of processing" or "workability") of the target superporous hydrogel.

However, it is important that the acidic treatment step involves treating the separated initial hydrogel material formed in step a) with at least one acidic material at a pH in the range <1 to ≤3, further preferably a pH in the range <1 to <3, highly preferably a pH in the range 1 to <3 and most preferably a pH in the range 1 to 2.8. The present Applicant has found it advantageous to use a pH in the range <1 to ≤3 in order to protonate the hydrogel and thereby achieve a greater pore size during the freeze-drying step. Additionally, we have observed that the final plasticised superporous hydrogels obtained by the present invention achieve the required rate and degree of expansion at low pH (e.g. in the stomach) and breakdown (when required) at high pH (e.g. in the duodenum).

It has been found that treatment of the initial hydrogel material with an acid solution of pH above 3 causes the target plasticised superporous hydrogel material, to lose its structural integrity, that is, a body of target superporous hydrogel (SPH) material which has been made from an initial hydrogel treated with an acidic solution of pH >3, loses its defined shape (this is especially evident in the case of cast moulded hydrogel material). Further the target superporous hydrogel also becomes less porous which in turn lowers the swelling rate. Specifically, the SPH body becomes progressively more distorted and less porous as the pH is increased from >3 to pH 9, it becomes very distorted at pH 10 and pH 11 and becomes a gelatinous mass or highly viscous fluid at pH 12 and beyond. Ideally, the acid solution used to treat the initial hydrogel comprises an aqueous solution of one or more acidic materials. The one or more acidic materials may be inorganic acids and/or organic acids.

Stronger acids are found to be more beneficial than weak acids, and materials with a pKa in the range −15 to 3.5 are preferred. A pKa in the range −15 to 3.0 is particularly preferred, a pKa in the range −15 to 2.5 is further preferred and a pKa in the range −15 to 1 is highly preferred. Suitable inorganic acids include hydrochloric acid, sulfuric acid, nitric acid and hydrofluoric acid. Suitable organic acids include citric acid, oxalic acid, tartaric acid, maleic acid, malic acid and toluene sulfonic acid. A 1-100 mM aqueous acidic solution is preferred, and further preferably an 80-90 mM aqueous acidic solution.

The one or more acidic materials may be derived from substances obtained or extracted from the animal or human body, or acidic materials made from compositions which simulate such substances, for example acidic solutions comprising gastric fluid and/or simulated gastric fluid are especially preferred. Simulated gastric fluid is preferably prepared without pepsin and preferably comprises 0.2%/wt sodium chloride and 0.7%/wt of hydrochloric acid per litre of water and has a pH of around 1.2.

Concurrently with the treatment of the initial hydrogel material with at least one acidic material as described above, or alternatively following said treatment, the initial hydrogel material is optionally further treated with a solution comprising one or more monovalent metal salts, preferably selected from salts of sodium, potassium and lithium. We have found that such metal salt treatment enables control over the plasticisation step which in turn determines the processibility of the target material and will ultimately affect the cost of manufacture.

Any water-soluble monovalent metal salt may be used, such as a chloride, bromide, iodide, nitrate, sulfate and carbonate. Sodium chloride and potassium chloride are particularly suitable. The presence of the monovalent metal salt solution is found to affect and advantageously control the processability (i.e. workability and handleability) of the final plasticised superporous hydrogel. In particular, the improvements in further processing and handling in the final superporous hydrogel are found to be proportional to monovalent metal salt concentration up to a maximum of 0.5M; at concentrations over 0.5M, the final plasticised superporous hydrogel becomes too soft to be worked easily within a reasonable timeframe (desirably from 1 minute to less than 60 minutes). Ideally, the monovalent metal salt solution will be a >0M to ≤1.5M solution, preferably it is a >0M to ≤1.25M solution, and further preferably it is a >0M to ≤1.14M solution.

In a particularly advantageous process of the present invention, the initial hydrogel material is treated with an acidic solution with a pH in the range 1 to 2, in addition to being treated with a <0.2M solution (preferably a 0.13M solution) of an alkali metal salt (particularly chloride), prior to being freeze dried to remove the solvent from the structure and to produce a dried superporous hydrogel material.

The initial hydrogel naturally comprises pores which are defined by the network/cross-linked structure, but these pores are filled with the solvent (e.g. the water) used in the polymerisation reaction to form the initial hydrogel material. In general, the more dilute the mixture of monomers/polymers from which the initial hydrogel is made, the larger the pore size. Typically, the initial hydrogel will have a density of around 1.30 g/cm³.

It is important that the resulting treated initial hydrogel is not allowed to dry out, for example at or above room temperature, as this will cause the treatment liquid(s) to evaporate too slowly from the swollen pores of the treated initial hydrogel material and any moisture in the structure will cause the pores to collapse; when the desired pores are lost, the swelling rate will be much reduced.

However, the target material is a plasticisted "super-porous" hydrogel material, thus it will typically have a pore volume of 70-90% and a typical density of around 0.7-0.8 g/cm³, therefore, it is necessary to enlarge/reveal the pores originally formed in the structure of the initial hydrogel (with a typical average size in their largest dimension of between 100 μm and 1000 μm and ideally between 200 μm and 500 μm) up to as large as 5 mm. It is key when enlarging the size of the pores, to form the required enlarged pore size and then "fix" this size as quickly and efficiently as possible, The initial hydrogel is therefore subjected to a freeze-drying process, either just after the step of treating with an acidic solution as described above, or if used, just after the step of treating with a solution comprising one or more monovalent metal salts. Advantageously, freeze drying is a fast and efficient drying process which removes the water, especially that which is held within the pores as mentioned above, quickly before the pores have had time to collapse.

The freeze-drying step is preferably carried out by first initial freezing of the acid (and optional monovalent metal) solution treated initial hydrogel in a conventional freezer or using an ultra-low temperature freezer (−20° C. to −86° C.), this crystalises and expands (e.g. by hydrogen bonding interactions) the liquid (preferably water) within the pores. The lower the temperature of freezing used in the initial freezing process, the smaller the crystals and the smaller the final pore size. The acid treated hydrogel samples are preferably placed in a mould which is larger by 1.5× to 2.5× the diameter of the pre-acid/metal salt treated initial hydrogel samples, before undergoing the initial freezing process. The frozen samples are then freeze-dried using freeze-drying apparatus (at −50° C. to −80° C.), until all of the inter-pore solution is removed, to yield a superporous hydrogel material with the desirable pore size (between 0.1 mm and 5 mm, preferably between 0.5 mm to 1.0 mm). It is highly preferred that the superporous hydrogel material made by the process of the present invention will preferably contain the same number of pores per unit weight as the initial hydrogel from which it is made.

An optional further step in the process of the present invention includes forming one or more through-holes which are preferably 1 mm to 15 mm in diameter, further preferably 3 to 6 mm in diameter, and highly preferably around 4 mm in diameter, in the body of the samples of superporous hydrogel material (prior to the plasticisation step discussed below). The ratio of the diameter of the through-hole : the diameter of a sample of the superporous hydrogel material is preferably from 0.75:1 to 1:30, further preferably from 0.5:1 to 1:10 and highly preferably 0.3: 1 to 1:10. Ideally, each of the one or more through-holes comprises a channel or conduit within the body of the sample of the superporous hydrogel that extends from a first opening in a first portion of the outer surface of the sample of superporous hydrogel to a second opening formed in a (preferably diametrically opposing) second portion of the outer surface of the sample of superporous hydrogel. Preferably the one or more through-holes are linear. For the avoidance of doubt, such "through-holes" are not formed directly as a result of the chemical polymerisation/crosslinking reactions which form the initial hydrogel, that is the "through holes" are not the pores formed between cross-linked interpenetrating backbones of the initial hydrogel material, instead such "through-holes" are formed as a result of a physical processing step.

In the case where the superporous hydrogel sample is a cylindrical body, the one or more through-holes are preferably formed to be aligned substantially parallel to the longitudinal axis of the sample. Non-cylindrical samples of superporous hydrogel preferably comprise one or more through-holes which are formed to be aligned substantially perpendicular to the direction in which a compressive force may be applied to the final plasticised superporous hydrogel, for example, during a further processing step to manipulate the plasticised superporous hydrogel into a dosage capsule, as discussed below. The through-holes may be formed using any suitable technique, for example the mould used to form the initial hydrogel sample may be embedded with or shaped to include one or more elongate members (e.g. elongated cylindrical members, pins or needles) aligned to be parallel with the central axis of the mound. Alternatively, the shape of the mould may be such as to allow a suitable through hole to be cast into the sample body when the initial hydrogel material body is formed. Further alternatively, the one or more through-holes may be drilled in the superporous hydrogel sample, for example using a 3-15 mm drill, and preferably at room temperature. Still further alternatively, each of the one or more through holes may be formed by extruding the initial hydrogel over a mandrel.

The effect of the one or more through-holes is to enable the final plasticised superporous hydrogel sample to be more easily compressed and folded upon application of a compressive force as discussed above. Additionally, the presence of through-holes also increases the surface area of the final plasticised superporous hydrogel sample and this promotes faster swelling (expansion) of the sample compared against a similar sample without one or more through-holes; further, a final plasticised superporous hydrogel sample with through-holes is found to be able to achieve a greater final swelling volume than a similar sample without through-holes (assuming each has a comparable dry volume) and this is important when the final plasticised superporous hydrogel material produced by the process of the present invention is used in a gastric retentive system.

The toughness of the final plasticised superporous hydrogel material is a particularly important characteristic which will have an impact on i) its ability to achieve a substantially unbroken/undamaged/non-compromised structure following compression (as discussed below), and ii) to ensure that the applied compressive force will be able to compress the sample effectively; a more highly plasticised superporous hydrogel will be more malleable and be able to withstand manipulations such as rolling/folding etc. without cracking. The dried superporous hydrogel material obtained by freeze drying an acid treated initial hydrogel material typically has a rigid and friable structure which needs to be altered to increase its plasticity, and, where desirable, enable insertion of the hydrogel material into a 000 size dosage capsule. The use of a plasticising agent (for example an ester such as a sebacate, an adipate, a terephthalate, a dibenzoate, a glutarate, a phthalate, a azelate, and blends thereof), may be one solution to this problem (either by adding such an agent to the reaction mixture from which the initial hydrogel is formed or by adding it to the initial hydrogel once formed), but this is generally undesirable, particularly although not exclusively, when the improved compressed hydrogel final product is to be used as a gastric appetite suppressant where the use of a minimal number of chemicals will reduce the risk of unwanted side effects. Thus highly preferably, alternative means are used to reduce the glass transition temperature of the superporous hydrogel and thereby increase its plasticity, prior to applying a compressive force. A favourable alternative means includes subjecting the freeze-dried superporous hydrogel to high humidity conditions (typically a percentage humidity of >55% to ≤100%, preferably a humidity in the range 65% to ≤100%), for example using water vapour (i.e. a damp environment), either at room temperature or, preferably, at an elevated temperature. The use of steam is beneficial. The length of time the freeze-dried superporous hydrogel is subjected to high humidity (water vapour and as described above) is critical for the performance of the resulting final plasticised superporous hydrogel material, and this duration is dependent on the original polymer composition of the initial hydrogel material (specifically, the cross linking density, the water content, and the amount of initiator), the size and shape of the dried superporous hydrogel sample/body, the molarity of the monovalent salt solution, and the processing methods used (including the freezing temperature and how the sample is frozen, i.e. within an open or sealed mould, the materials of the mould etc.). A water vapour treatment step is preferably performed in a lidded container which contains a small amount of water and is heated to between 50 and 65° C. (preferably 60° C.) to generate the required % level of humidity within (as described above). It is important to prevent condensation of the water vapour, for example on the inside surfaces of the walls or the lid of the container, because if the sample of superporous hydrogel comes into contact with any water droplets (or even visible water vapour) during plasticisation it will cause the sample to irreversibly deform, primarily by the collapse of the porous structure, and this will cause the final product to completely fail to expand. Consequently, the surface of the inner wall of the lidded container preferably includes a covering of a wetted absorbent material; this not only assists to provide an even level of humidity within the container but also mitigates against drips of condensed water forming and falling/running onto the superporous hydrogel sample. A sample of the superporous hydrogel is placed in the container and the container is tightly sealed with the lid. The sample is then retained in the container for a desired period, and then immediately removed from the container and subjected to mechanical processing/manipulation, as described below. If the superporous hydrogel is treated with water vapour for too long, it will lead to irreversible deformation (primarily shrinking), while under-treatment will result in insufficient plasticising of the sample of superporous hydrogel. In the case of the former, it is unlikely to be possible to compress the hydrogel successfully as it may become elastic and spring back to its original shape when the compression force is released. For the latter case, further mechanical processing is likely to break the structure of the sample. One of the useful advantages of treating the initial hydrogel with an acidic solution is that the duration needed for water vapour treatment is reduced. For example, at 60° C. the typical vapour treatment time when the initial hydrogel has been acid treated at pH1-3 is from 5 to 20 minutes, (preferably from 5 to 12 minutes), whereas an otherwise identical a sample of initial hydrogel which has not been treated with an acidic solution, will require water vapour treatment for >20 to 60 minutes or even longer to achieve a comparable degree of plasticisation. Treatment of the initial hydrogel materials with a monovalent metal salt solution, either at the same time or after treatment with an acidic solution, enables still further control over the duration of water vapour treatment. The present applicant has found that a monovalent metal salt and acid treated material needs only be treated under high humidity conditions (water vapour), at 60° C., for between 1 and up to 5 minutes, and highly preferably 3 minutes).

Another useful advantage of treating the initial sample of hydrogel with an acidic solution is that the acid solution treated initial hydrogel material will have larger and better connected pores than a non-acid treated sample; such larger and better connected pores are more permeable and result in more efficient water absorption, i.e. such materials exhibit faster swelling and higher swelling volume, as demonstrated below in the specific examples. Moreover, during an acid treatment step the gel is caused to swell slightly in all directions, and as a result of this swelling, more water can penetrate the polymeric network and the pores of the material are expanded. When this slightly swollen (expanded/water entrained) material is frozen and then freeze-dried, the pores remain at their expanded size.

Once the superporous hydrogel is sufficiently plasticised, the sample is handled under appropriate humidity and temperature conditions to prevent hardening. The process of the present invention then involves the application of a compressive force, preferably with at least a component force in a radial direction. In some instances, it is desirable to form a thin sheet of plasticised superporous hydrogel by reducing the initial thickness of the plasticised superporous hydrogel to 50% or less, preferably 30% or less and highly preferably 15% or less of the initial thickness, (i.e. the thickness of the initial hydrogel is reduced by at least 50%, preferably by at least 70% and highly preferably by at least 85%, respectively, following compression).

The application of the compressive force collapses/flattens the pores in the plasticised superporous hydrogel, and is effected by applying a compressive force using any suitable means or apparatus, for example between one or more pairs of rollers and/or use one or more plates to exert pressure and/or use a vacuum to assist in providing the at least partially radial compressive force. Once formed the plasticised superporous hydrogel sheet may be rolled, folded, pleated, corrugated, spooled, concertinaed, cut, extruded and moulded, prior to it being inserted into an oral dosage capsule, as described in WO2019016560 (A1).

In the case of a moulded plasticised superporous hydrogel material, the present Applicant has found that it is beneficial to manipulate (e.g. fold, and/or squash) the moulded plasticised superporous hydrogel material as formed (i.e. directly without forming a sheet first), for example to insert it into an oral dosage capsule. As described above the initial hydrogel material may be moulded into any desired shape. In the case where the initial hydrogel, and hence the plasticised superporous hydrogel, is a cylindrical sample, it is desirable to form one or more through-holes or channels within the body of the superporous hydrogel as described above. A compressive force may then be applied to the plasticised superporous hydrogel, preferably in either a radial or a combined radial and axial direction, in relation to the longitudinal axis of the moulded plasticised superporous hydrogel material. In a preferred example, the compressive force may be applied to a moulded plasticised superporous hydrogel material using an elongate rod (for example of outside diameter 3 to 15 mm (preferably 6 to 10 mm)) with its longitudinal axis oriented parallel with the central longitudinal axis of the hydrogel sample (i.e. parallel with the one or more through-holes, if present), to create a linear depression or compressed line in the lateral side of the outer surface of the plasticised superporous hydrogel sample. The cylindrical sample is then able to be folded along this compressed line to form a "quasi"-cylinder which may be squashed using trilateral compression. Such trilateral compression (which mainly involves opposing biaxial forces with a minor component of force in the third axis) may be performed, for example, by inserting the quasi-cylindrical sample of folded plasticised superporous hydrogel into a hollow tapered tube and then pushing it along inside the tube to shape and compress it further and to reduce its diameter to a desirable size (e.g. a capsule diameter). The sample/capsule may preferably be left for 2-10 min (preferably 4-6 min) for the complete fixation of the shape before it is pushed out of an open end in the tapered tube (preferably with an internal diameter of 26 mm). Alternatively, the folded sample may be pushed into a cylindrical tube (for example with an internal diameter of 8 to 13, preferably 9-10 mm) with two opposing open ends. Two push rods each with a concave shaped end may be inserted, one into each of the two open ends of the cylindrical tube, with their concave shaped ends being used to simultaneously squeeze the folded sample on opposing sides and, thereby, form a lozenge-shaped compressed superporous hydrogel-containing capsule with the rounded dome-shaped ends. It is also possible for the plasticised superporous hydrogel material to be moulded (squashed) directly into a dosage capsule mould.

The folding step is most preferably performed on samples which comprise one or more through-holes as they exhibit particularly high diameter swelling-ratios.

As described above, the preparation of the superporous hydrogel material involves washing the initial hydrogel with an acidic solution followed by the optional treatment with a monovalent salt solution, means that it may not be necessary to form one or more through-holes, and consequently no need to fold the sample of superporous hydrogel material along a compressed line as described above. Ideally, the plasticised superporous hydrogel samples can simply be trilaterally compressed for example by squeezing them directly into a capsule mould or a gelatine capsule shell or one of the tapered or cylindrical tubes described above.

It is preferable that the compressive forces are applied at an elevated temperature since a material is more easily deformed by an external force at a temperature above its glass transition temperature (Tg) Following application of the compressive forces, as mentioned above, the elevated temperature may be reduced, for example to ambient temperature, to "set" the shape of the compressed plasticised superporous hydrogel. Further, after mechanical processing, it is preferred that any remaining moisture in the compressed plasticised superporous hydrogel capsule is removed, therefore the product is preferably further dried (e.g in a desiccator or by re-freeze drying) to ensure long-term storage stability.

The above compositions are ideally suited to provide a product formulation comprising a plasticised superporous hydrogel material prepared by the process of the present invention, optionally in compressed form, and optionally together with one or more slow swelling non-superporous hydrogels. Preferably, the product formulation will be suitable for use as an appetite suppressant, for example to control of weight gain and to prevent obesity, or to deliver a pharmaceutical and/or nutraceutical to within a human or animal body.

The size of the product formulation (such as a capsule, tablet or lozenge) is preferably a standard 000 capsule or other form of capsule and the insertion of the improved superporous hydrogel prepared by the process of the present invention is preferably achieved as described above.

In many applications it will be important that each plasticised superporous hydrogel material-containing capsule can swell to a size which is larger than the diameter of the pylori of the patient (human or animals) to ensure its retention in the stomach.

Whilst the product formulations of the present invention are designed not to block the oesophagus or lower GI tract, it is possible that an unforeseen accident may happen. Also, it is desirable that the appetite suppressant formulation can be terminated easily without the need for surgical, endoscopic or other unpleasant medical interventions. The present invention combats these issues using a trigger or emergency exiting mechanism to breakdown of the product formulation into a form which is easily excreted by the patient. The 'breakdown trigger' can have variety of forms so long as it is effective and efficient in the breakdown process and is safe to be used by the patient, Preferred breakdown triggers include, electromagnetic waves (e.g. light, heat), mechanical waves (e.g. ultrasound) or chemicals.

Depending the nature of the hydrogel, the breakdown trigger could be, but is not limited to, one of the following:

(1) a solution with certain chemical or chemicals which attack the crosslinking groups;

(2) an alkaline solution which reduces the mechanical strength of a pH-sensitive hydrogel;

(3) a high intensity focused ultrasound (HIFU) device that targets hydrogel-containing compositions;

(4) a heat, light, electrical signal delivered to the blockage point by endoscopic or another capsule like device that will trigger the response of temperature-, light-, electricity-sensitive hydrogels.

As an Example, hydrogels of the present invention can be designed to have reversible crosslinking that can be attacked by certain chemicals. Whilst the reversible crosslinks will be stable in the stomach environment, the chemical trigger is preferably either something that is not normally consumed in daily life or something that exists in food but in an amount which is too low to cause an immediate breakdown of the hydrogel. The quantity and concentration should be strictly controlled within the allowance that can be found in the regulations given by the established authorities. The potential reversible crosslinking and their antidotes might include one or more of the following in Table 1:

The improved compressed plasticised superporous hydrogel material prepared by the process of the present invention may be used in the treatment and/or prevention of one or more medical conditions which can include, but are not limited to, obesity and diabetes. Highly preferably, such hydrogel may be used as an appetite suppressant.

In a further aspect, the present invention provides dosage regimen for administering to a patient suffering from one or more medical conditions, for example selected from obesity and diabetes, comprising orally administering to the patient a first dose of an orally acceptable formulation comprising the high-volume swelling hydrogel of the present invention in an amount of or a number of samples which will swell upon ingestion to fill up to 80%, preferably up to 60%, further preferably up to 50% of the volume of the stomach of the patient.

In a preferred dosage regimen for treating an obese or diabetic patient, an initial large first dose of preferably greater than 3, preferably at least 5 and further preferably at least 20 orally acceptable tablets or capsules (any other suitable product formulation may also be used, preferably 000 size capsules) comprising one or more high-volume swelling hydrogels of the present invention are administered to the patient. This is then optionally followed by a second, and optionally further subsequent, doses preferably containing up to 5 orally acceptable tablets or capsules (or any other suitable product formulation) which comprise one or more high-volume swelling hydrogels (these may be the same or different from those in taken in the initial high dose) at time intervals of around at least 12 hours and preferably around at least 24 hours, and highly preferably longer e.g. around 48 hours. Preferably, the high-volume swelling hydrogel-containing product formulation will be retained within the patient's stomach for several days (1-7 days), further preferably for several weeks (1-30 weeks) or even longer. The optional second and subsequent doses may be the same as or different from each other.

Ideally the above method will also include the ingestion by the patient of around 200 ml of water (preferably tepid, further preferably at around 37° C.), before and/or during and/or after the ingestion of the at least one of the first, second or further subsequent doses by the patient.

TABLE 1

| Hydrogel base | Crosslinking agent | Reversible bonding | Potential Breakdown Triggers |
|---|---|---|---|
| Acrylamide | N,N'-bis(acryloyl)cystamine (BAC) | Disulfate bonds | Glutathione/ Cysteine-HCl/ Lycopene/ Procyanidine |
| N-isopropyl-acrylamide | N,N'-bis(acryloyl)cystine (BISS) | Disulfate bonds | Glutathione/ Cysteine-HCl/ Lycopene/ Procyanidine |
| Alginate | Calcium chloride, Calcium sulphate | Calcium centred ironical bonding | Ethylenediamine-tetraacetic acid & its salts Porphine/heme/ Chlorophyll or any strong calcium binding/chelating agent. |
| poly-(di(carboxylatophenoxy)phosphazene) | Calcium chloride, Calcium sulphate | Calcium centred ironical bonding | Ethylenediamine-tetraacetic acid & its salts Porphine/heme/ Chlorophyll etc. |

A further separate and independent invention provides a similar process for making a body of plasticised superporous hydrogel material as described above, which includes a through-hole forming step, optionally includes a monovalent metal salt treatment step, but does not include an acid treatment step. The through-hole treatment step is found to be especially useful because non-acidic solution treated materials are generally less yielding than their acid-treated counterparts, and the use of the through hole enables the moulded or non-moulded final plasticised superporous hydrogel material to be folded/rolled into a desired shape for insertion into a 000 dosage capsule. Save the lack of acid treatment, all other steps, features and advantages as described above, will apply to this separate invention.

DESCRIPTION OF THE DRAWINGS

The invention will now be described with reference to the representations in the following Figures, in which.

SPECIFIC EXAMPLES

The abbreviations used herein are defined as follows:

TABLE 2

| Abbreviation | Chemical |
|---|---|
| AAm | Acrylamide |
| AL | Alginic acid sodium salt |
| APS | Ammonium persulfate, |
| BAC | N,N' bis(acryloyl)cystamine |
| $CaSO_4$ | Calcium sulfate dihydrate |
| Cellulose | Cellulose |
| DW | Distilled water |
| TEMED | N,N,N',N'-tetramethylethylenediamine |
| SGF | Simulated gastric fluid without pepsin (0.2%/wt sodium chloride and 0.7%/wt hydrochloric acid solution; pH = 1.2) |

EXAMPLE 1: (CONTROL)

Example 1: (Control) The Preparation of Plasticised Superporous Hydrogel Material (PSH) with One or More Through-Holes Formed Therein to Assist in the Folding of the PSH to Reduce its Size and to Facilitate the Preparation of an Oral Dosage Formulation Synthesis and Polymerization 16.0 g (+/−0.1 g) of AAm and 99.0-132.0 mg (+/−1 mg) BAC were weighed and mixed with 90-200 ml of DW. Meanwhile, 20.0 g (+/−0.5 g) of AAm into a 6.0 g (+/−0.1 g) AL were weighed and mixed with 160-290 ml of DW. The above two solutions were mixed together with 433.0-751.0 mg (+/−1.0 mg) of APS, and the resulted solution was equally distributed into 8 smaller beakers (marked as Group A).

Into each of another 8 beakers (marked as Group B) was weighed 150.0 mg (+/−1.0 mg) of $CaSO_4$ powder, 6.2 ml water and 47-82 ul TEMED.

Figure 1A:
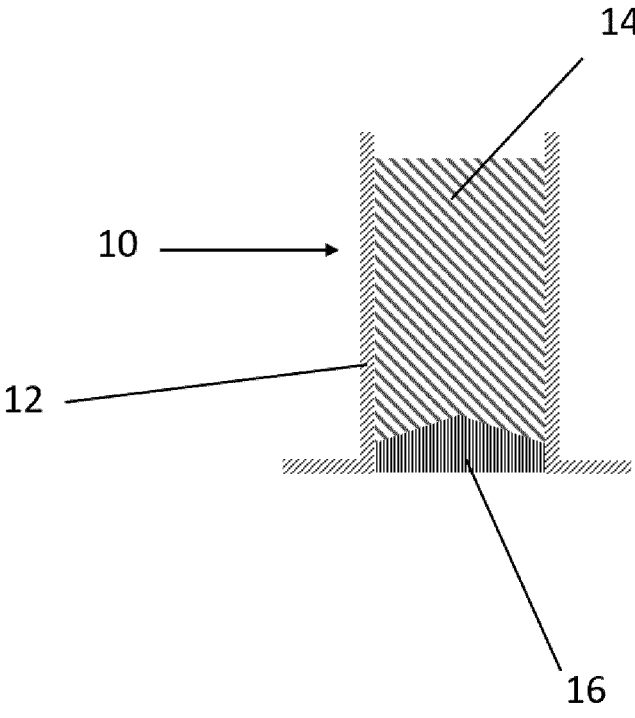
FIG. 1A: shows a cross-sectional view of a mould containing an initial hydrogel material prior to sealing.
Figure 1B:
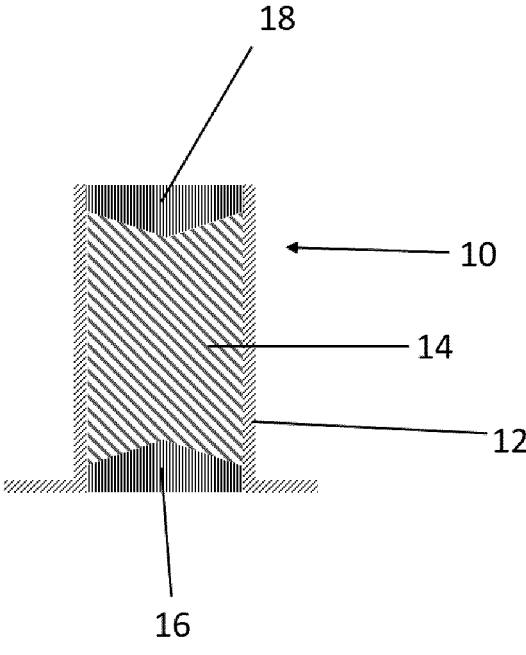
FIG. 1B: shows the same cross-sectional view of the same mould depicted in FIG. 1A after sealing.

The solution in one of the 8 beakers in Group A was poured into with the suspension in one of 8 beakers in Group B. The mixture (14) was then stirred for 10-50 seconds and poured into 4-8 moulds (10). Each mould consisted of a cylindrical polypropylene (PP) tube (12) with an internal diameter of 10-40 mm and top and bottom matching conical rubber stoppers (16, 18) with the same external diameter. The rubber stoppers (16, 18) in the tube mould (10) as shown in FIGS. 1A and 1B.

Similar operations were repeated for all 8 sets of solutions in Groups A & B, and all the samples in the PP moulds (10) were left in an incubator (preheated to 60° C.) for 1 hour. The moulds (10) were then transferred into a humid chamber to cure for another 24-72 hours at room temperature for the completion of polymerization. The resulting gelled materials (initial hydrogel materials) were labelled as the as-prepared gels (APGs).

Freezing & Freeze-Drying

The APG gels in their respective mould (both ends of which were sealed with rubber stoppers), were left in a –20° C. freezer for 8-24 hours and then transferred into the freeze-dryer to remove the water from the frozen gels over a period of 48 to 72 hours. This produced freeze-dried superporous porous hydrogel (a freeze-dried SPH).

Formation of Through-Holes

One or more through-holes or channels of diameter 4 to 10 mm were drilled along the longitudinal axis of each cylindrical sample of freeze-dried SPH to form a drilled freeze-dried SPH. The swarf was blown off, for example using a fan.

Plasticisation

A lidded container half filled with water and including a sample holder which could float on the water in the container were left in the incubator of 60° C. for 24 hours. A sample of drilled freeze-dried SPH was then put in the sample holder and left inside the container for 30 to 60 min until it became malleable.

Compression

Figure 2A:
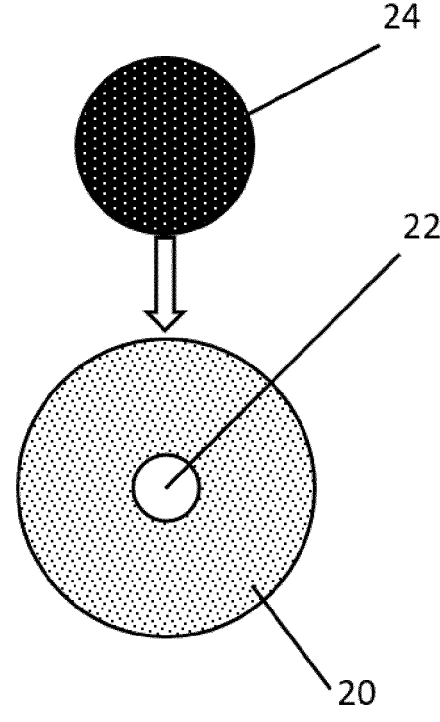
FIG. 2A: shows an end-on view looking at the circular end surface of a cylindrical sample of plasticised superporous hydrogel drilled with a through-hole along its central longitudinal axis, and the circular end surface of a cylindrical compression rod prior to it being used to compress the hydrogel sample.
Figure 2B:
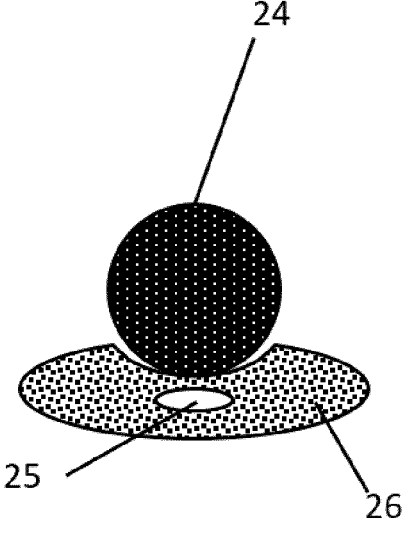
FIG. 2B: shows a cylindrical compression rod being used to compress the cylindrical sample of plasticised superporous hydrogel depicted in FIG. 2A.
Figure 2C:
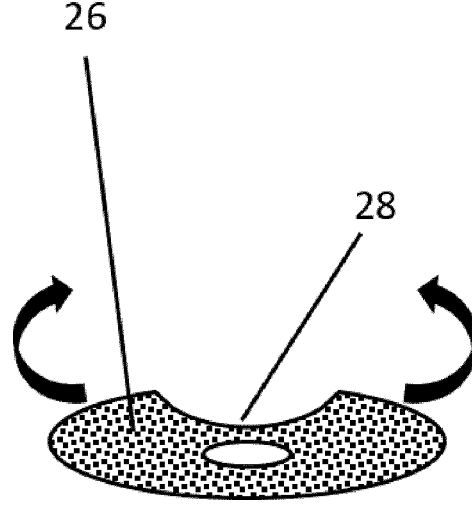
FIG. 2C: shows the cylindrical sample of plasticised superporous hydrogel depicted in FIG. 2B about to be folded in the direction of the arrows using the compression fold made in its surface by the cylindrical compression rod (removed)
Figure 2D:
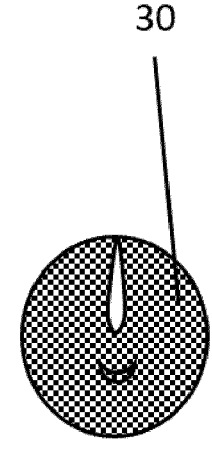
FIG. 2D: shows the cylindrical sample of plasticised superporous hydrogel depicted in FIG. 2C after folding to reduce its diameter.
Figure 3:
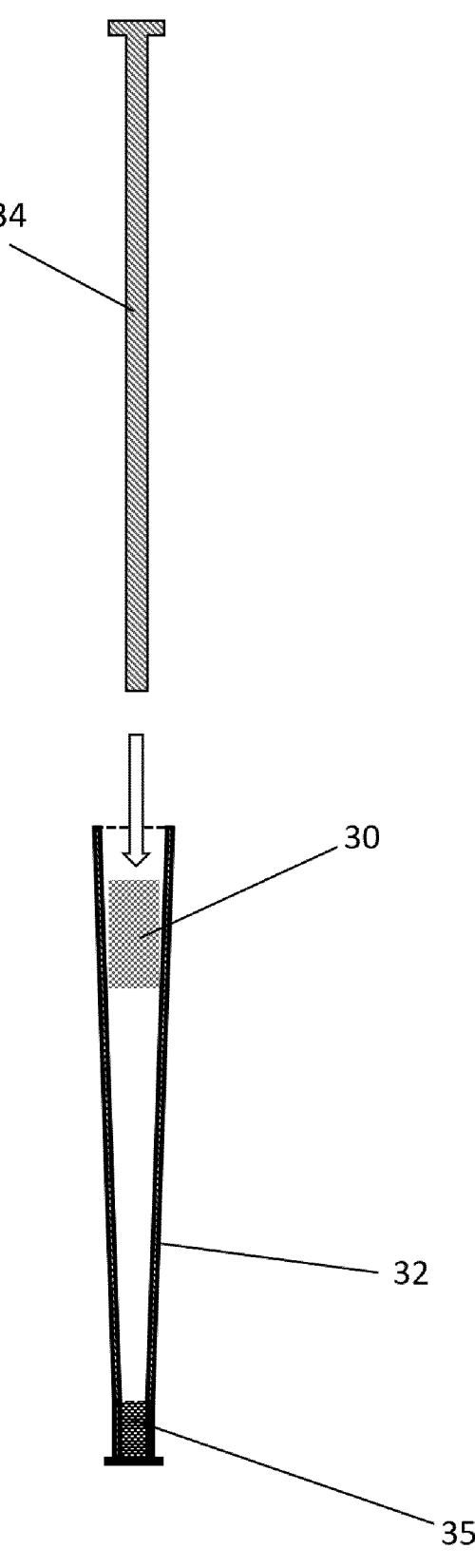
FIG. 3: shows a cross-sectional view of two folded cylindrical samples of plasticised superporous hydrogel inserted into a hollow tapered cylindrical mould and a push rod.
Figure 4A:
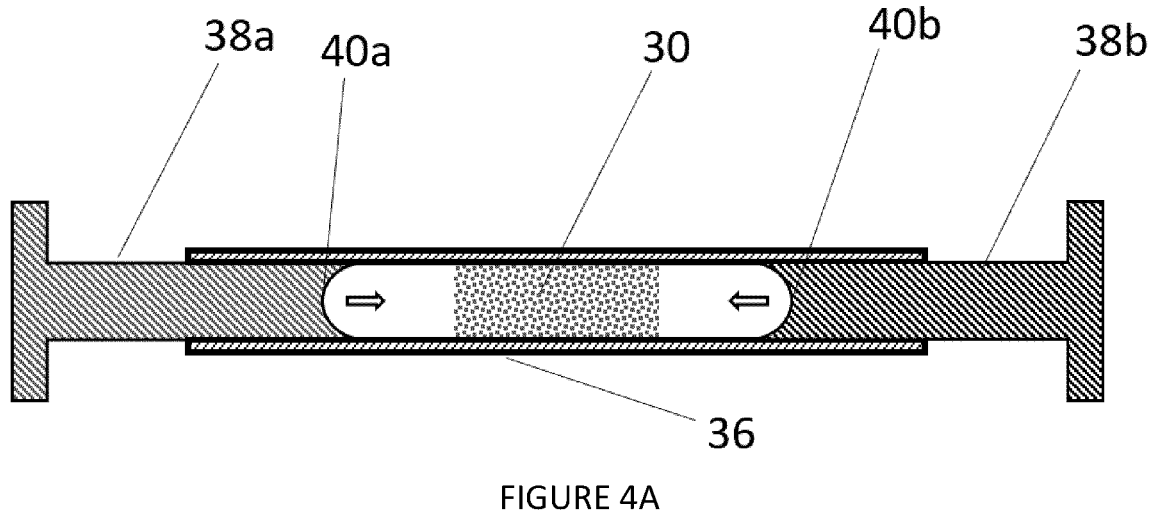
FIG. 4A: shows a cross-sectional view of a folded cylindrical sample of plasticised superporous hydrogel inserted into a hollow open-ended cylindrical mould with two push rod, one inserted in each of the two open ends of the mould.
Figure 4B:
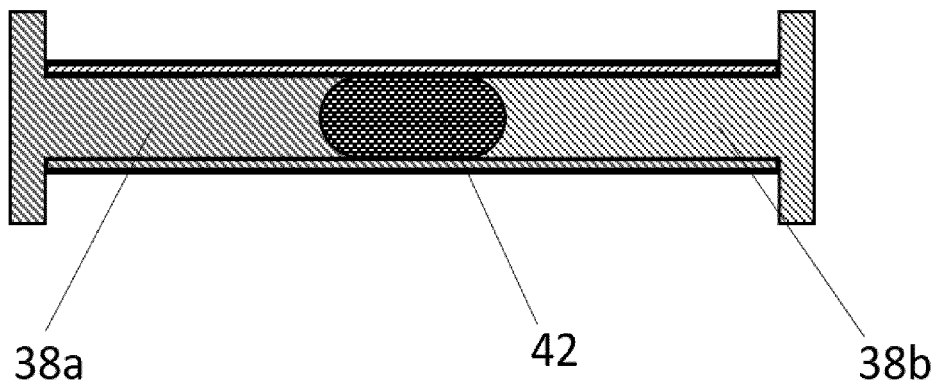
FIG. 4B: shows a cross-sectional view of the folded cylindrical sample of plasticised superporous hydrogel inserted into a hollow open-ended cylindrical mould as shown in FIG. 4A, with the two push rods compressing the sample on opposing sides.

The malleable (plasticised) drilled freeze-dried SPH (20, 26)) was carefully removed from the container and compressed along the hole (22, 25)) from the lateral side of the sample with a rod (24), folded along the compressed line (28) to form a folded plasticised drilled freeze-dried SPH (30) as shown in FIG. 2D, and then either squeezed through an open-ended tapered tube to reduce its size to that of an oral dosage capsule, as sown in FIG. 3, or squeezed into a cylindrical tube and compressed with push rods (38a and 38b), each having a concave end (40a, 40b) and each inserted into opposing open ends of the cylindrical tube (36), as shown in FIGS. 4A and 4B, or directly moulded in a capsule mould.

Example 2: The Preparation of a Superporous Hydrogel Material Using the Process of the Present Invention Using an Acidic Solution to Treat the Precursor Initial Hydrogel Material and Forming One or More Through-Holes in the Body of the Sample when at the Superporous Hydrogel (SH) Stage to Further Assist Processing the PSH Material into a Lozenge-Shaped Shaped Body The synthesis and polymerisation step used in Example 2 to form the initial hydrogel material, was exactly the same as used in Example 1.

Treatment with an Acidic Solution

The rubber stoppers (16, 18) were removed from the mould (10) shown in FIG. 1B, and DW was used to wet the interface between the APGs and the PP tubes (12) so that the APGs could slide out from the tubes for the next washing process.

The APGs were submerged in SGF (at a pH of around 1.3) for 7-14 days with a daily routine of flushing the samples and containers with DW as well as refreshing of the SGF. The volume of the SGF used to soak the samples was 15~50 ml per gel.

Freezing & Freeze-Drying

The expanded and acidic solution washed samples were drained from the SGF, and each hydrogel was directly put into a PP cylindrical tube mould which has a similar diameter to that of a swollen gel. The swollen gel inside the mould was then put into a –20° C. freezer for 8-24 hours and then transferred into the freeze-dryer to produce a freeze-dried superporous hydrogel (freeze-dried SPH).

Formation of Through-Holes

One or more through-holes or channels of diameter 4 to 10 mm were drilled along the longitudinal axis of each cylindrical sample of freeze-dried SPH to form a drilled freeze-dried SPH. The swarf was blown off, for example using a fan.

Plasticisation

A lidded container half-filled with water and including a sample holder which could float on the water in the container were left in the incubator of 60° C. for 24 hours to ensure a uniform temperature. The freeze-dried SPH with a hole was then put in the sample holder and left inside the container for 5 to 20 min until it became malleable.

Compression

Figure 4C:
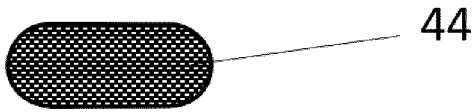
FIG. 4C: shows the sample of compressed folded plasticised superporous hydrogel shown in FIG. 4B following demoulding from the hollow open-ended cylindrical mould.

The malleable (plasticised) freeze-dried SPH sample was carefully removed from the container and as shown in FIGS. 2A and 2B compressed along the hole (22) from the lateral side of the sample (20) with a rod (24) and folded along the compressed line as shown in FIGS. 2C and 2D and the resulting folded sample (30) of plasticised freeze dried super porous hydrogel was squeezed, as shown in FIG. 4A, into a cylindrical tube (36) with an I.D of 9~10 mm. Two studs (38a and 38b) (O.D 9~10 mm) with a specially made dome concave on one end (40a and 40b) were put on either side of the sample (30) in the tube (36) and were pushed towards the centre to form the round ended hydrogel capsule (42) which was then removed from the tube as free capsule (lozenge-shaped body) (44) as shown in FIG. 4C.

Results

The degree of swelling can be measured in several different ways, for example:
1) by recording the change in size by placing the samples before and after swelling on a calibrated grid (1 cm squares).
2) using a displacement method in which the initial volume of a dry gel is first measured using an ethanol displacement method. The gel is put in a measuring cylinder filled with pure ethanol and is pushed down by a thin needle to just submerge the ethanol. The displacement of the liquid level is calculated and taken as the initial volume of the dry gel. When the amount of displaced ethanol is measured, the gel is removed from the ethanol, dried (for example using a clean tissue) and left in the fume hood for 1 hour to evaporate the remaining ethanol before the gel sample is put in a swelling media (e.g. water or SGF). Upon completion of swelling, the swollen gel volume is determined using the same liquid-displacement method as immediately mentioned above but using the swelling medium as the liquid in place of the ethanol. The difference between the volume of displaced ethanol and the volume of displaced swelling liquid is used to determine the swelling volume ratio for the gel.

3) measuring the length and diameter of hydrogel samples before, and after swelling using callipers.

Examples 1 and 2 both produced compressed plasticised superporous hydrogel materials, however the material produced in Example 2 (#NG) achieved faster-swelling results with the maximum swelling size being achieved in around 20 min (in SGF and water), as compared against the hydrogel made using Example 1 (#OG) which needed more than 60 minutes to achieve the same degree of swelling.

Summary of the Results

TABLE 3

Figure 5:
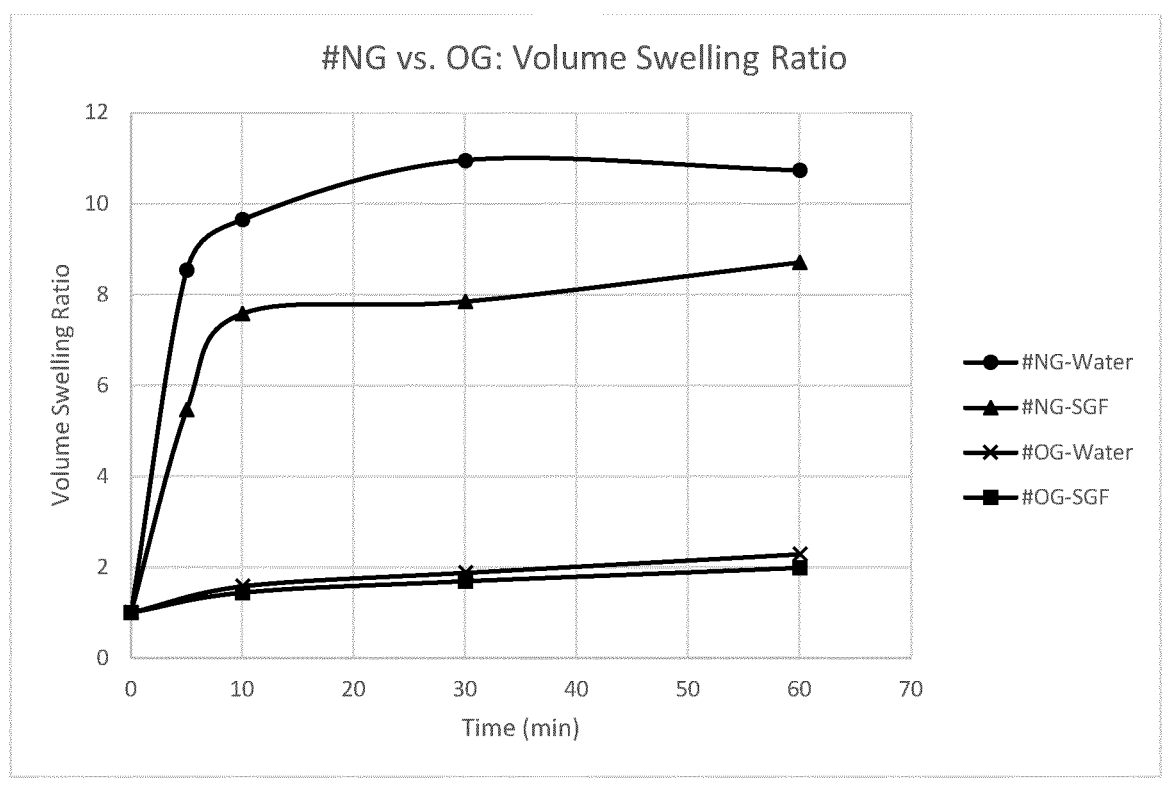
FIG. 5: shows a graph of the volume swelling ratio versus time, using either water or simulated gastric fluid as the swelling medium, for the compressed folded plasticised superporous materials produced according to the control Example 1 (#OG) and the present invention present invention in Example 2 (#NG)
Figure 6:
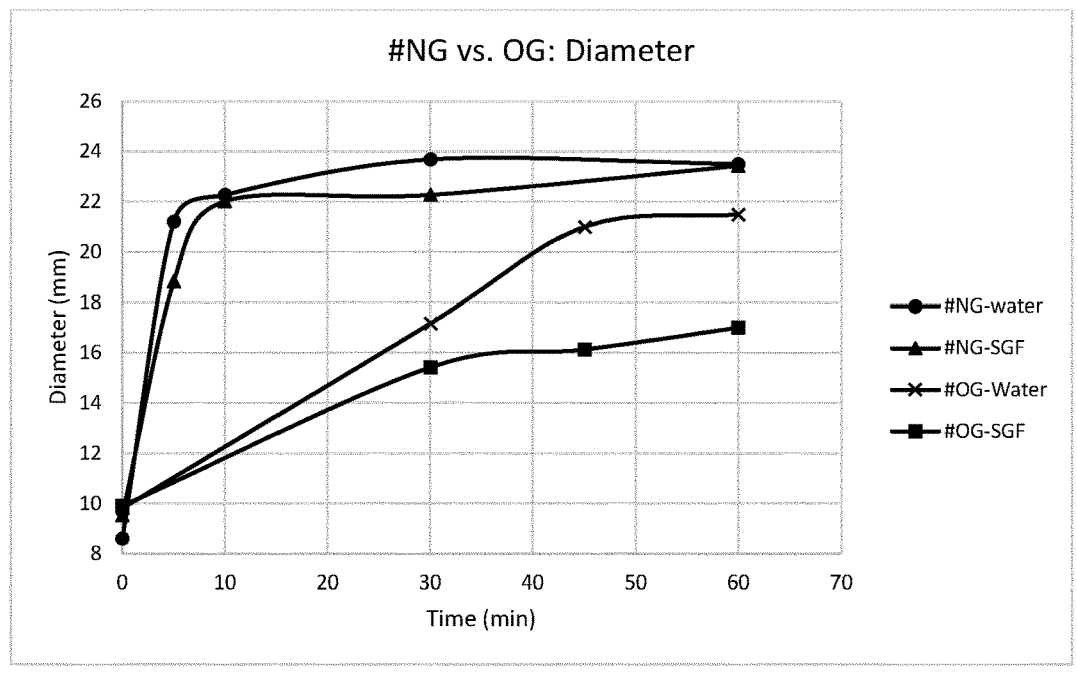
FIG. 6: shows a graph of the swelling diameter profile against time, using either water or simulated gastric fluid as the swelling medium, for the compressed folded plasticised superporous materials produced according to the control Example 1 (#OG) and the present invention Examples 2 (#NG)
Figure 7:
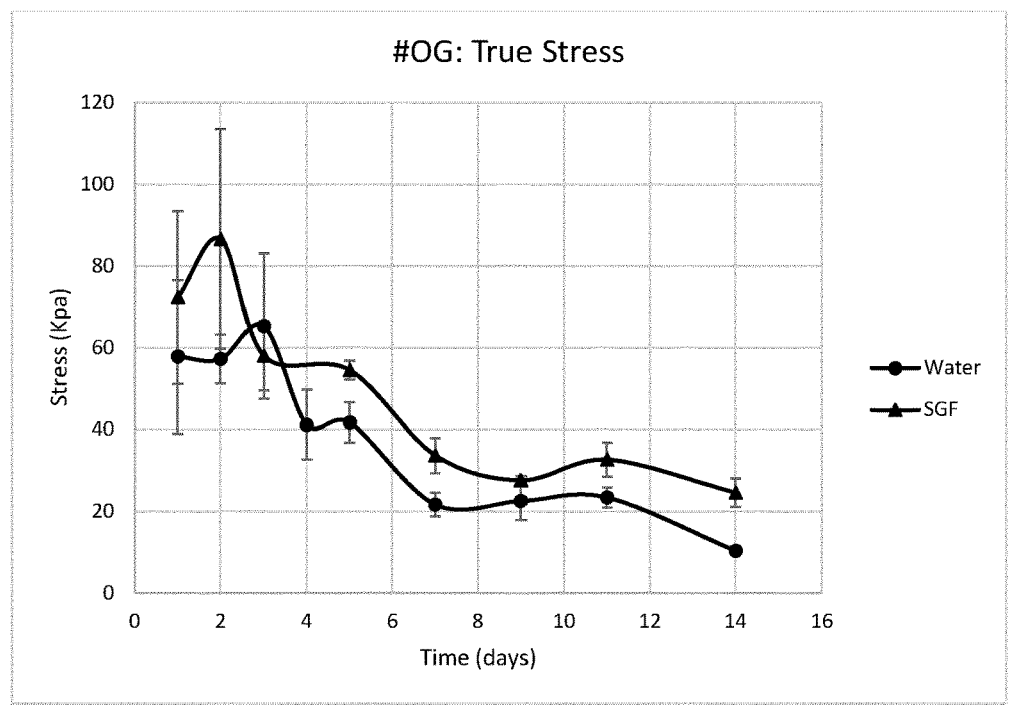
FIG. 7: shows a graph of true stress versus time, using either water or simulated gastric fluid as the swelling medium, for the compressed folded plasticised superporous material produced according to the control Example 1 (#OG)
Figure 8:
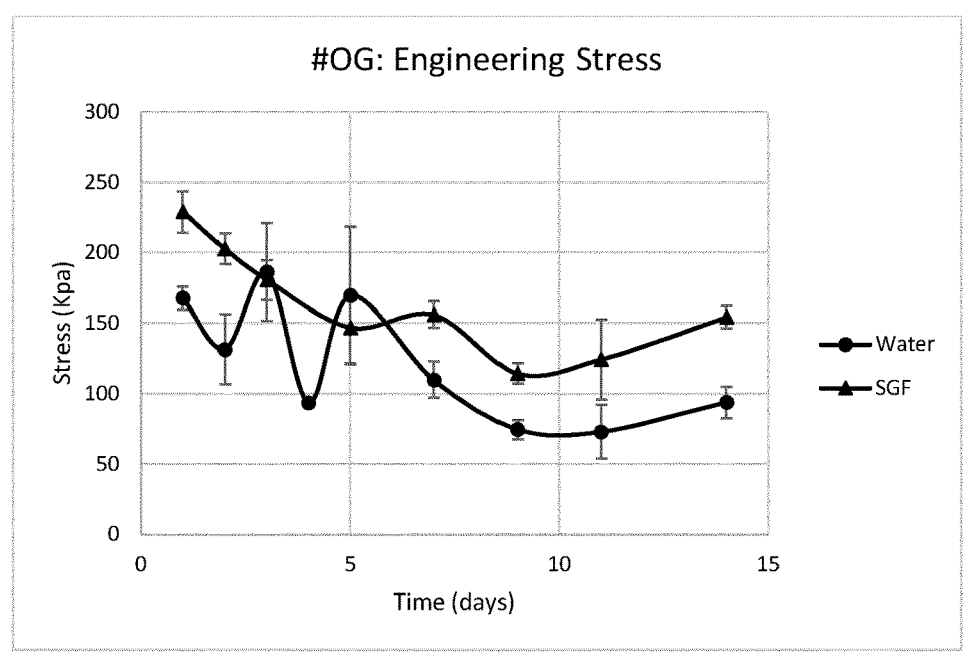
FIG. 8: shows a graph of engineering stress versus time, using either water or simulated gastric fluid as the swelling medium, for the compressed folded plasticised superporous material produced according to the control Example 1 (#OG)
Figure 9:
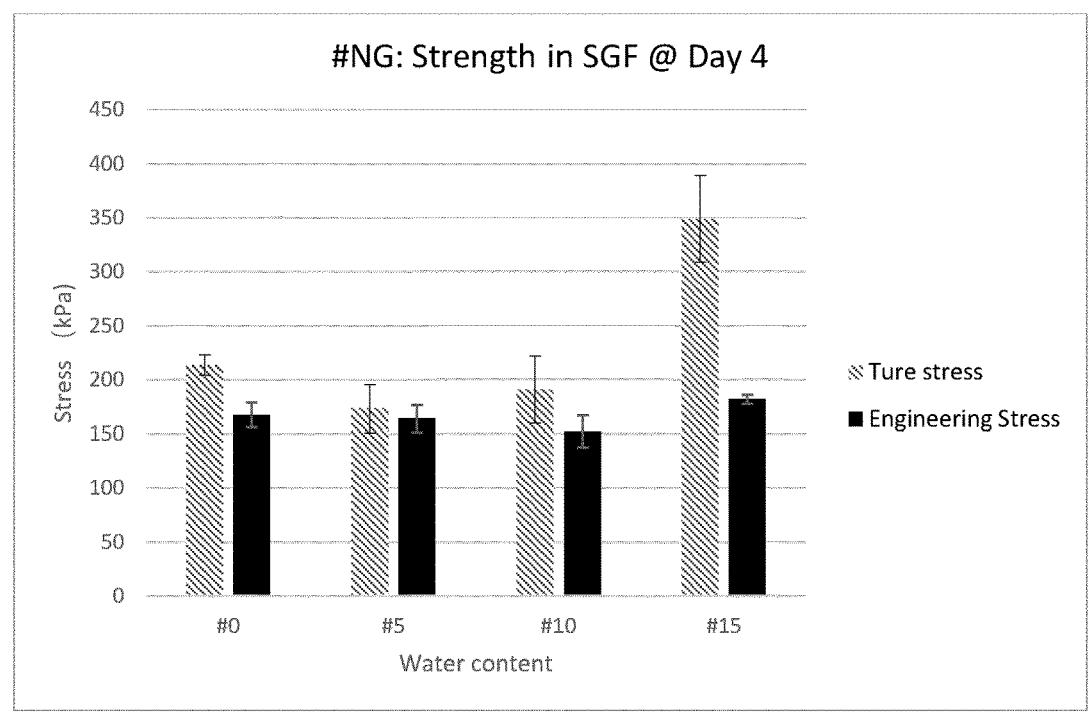
FIG. 9: shows a bar graph showing the 4-day strength in simulated gastric fluid of the compressed folded plasticised superporous material produced according to the present invention in Example 2 (#NG).

| | SUPERPOROUS HYDROGEL MADE USING CONTROL EXAMPLE 1 (#OG) | SUPERPOROUS HYDROGEL MADE USING EXAMPLE 2 (#NG) |
|---|---|---|
| Swelling rate | Fast-swelling: can swell to the critical size (>20 mm in diameter) within 60 min in water | Superfast-swelling: Swelled to 8-10X in 10 min; can swell to >25 mm in 20 min in both water and SGF |
| Volume Swelling ratio | Volume swelling ratio of 18-20X in water (14 days) 8-12X in SGF (14 days) (See FIG. 5) | Volume swelling ratio of 10-12X in both water and SGF (1 day) (See FIG. 5) |
| pH sensitivity (The effect of pH on swelling ratio) | The swelling ratio is1.5-2.5X larger in water (pH 7) than SGF (pH 1.2) The time taken to get to 15% volume increase is faster in water when compared to the time for SGF solution) | pH has no effect on either the swelling rate or the swelling ratio |
| Mechanical property | Elastic; less flexible; water cannot be squeezed out. Engineering stress at the point of breaking (measured using a force meter calibrated in pressure units) 60N (168 kPa) −> 27N(94 kPa) from day 1 −> day 14 in water 82N(229 kPa) −> 45N(154 kPa) from day 1 −> day 14 in SGF; 73N (180 kPa) @ Day 3 in SGF (See FIG. 8) Max True stress at breaking point (measured using a force meter) 7.7N(58 kPa) −> 1.4N(10 kPa) from day 1 to day 14 in water; 9.6N(72 kPa) −> 3.3N(25 kPa) in SGF 7.7N (58 kPa) @ Day 3 in SGF (see FIG. 7) | Spongy; more flexible compared with the material of Example 1; lower elastic modulus (as determined by the observed ease of compression as measured by a force meter) (deform more upon compression); water can be squeezed out Engineering stress at the point of breaking (measured using a force meter calibrated in pressure units) 81N (182 kPa) @Day 4 in SGF Similar results are observed in water Max True stress at breaking point (measured using a force meter) 46N (349 kPa) @Day 4 in SGF (see FIG. 9) |
| Processing | Steaming time: 30 min Lead time: 27-30 days | Steaming time: 5-15 min Lead time: 15 days |
| Potentials | — | Can be made less spongy by using less water initially without compromising the fast-swelling ability; Can change the freezing method (sealing) to change the crystal structure and pore size to slow down the initial swelling rate. |

Example 3: Experiment to Investigate the Effect of pH on the Appearance and Swelling Performance of Plasticised Superporous Hydrogel Material Made by the Process of the Present Invention The synthesis and polymerisation step used in control Example 1 was used to prepare thirteen (13) separate samples of initial hydrogel material, each individually cast in a mould (10). Each moulded sample was then treated in accordance with the present invention, as follows.

Treatment with an Acidic Solution

The rubber stoppers (16, 18) were removed from each mould (10) shown in FIG. 1B, and DW was used to wet the interface between the APGs and the PP tubes (12) so that the APGs could slide out from the tubes for the next washing process.

Each of the APG samples was submerged in its own acidic solution, with a different pH for each and being between pH 1 and 12, and the thirteen APG sample being submerged in SGF (at a pH of around 1.3), for 7days. The volume of the acidic solution used to soak the samples was 15~50 ml per gel.

Freezing & Freeze-Drying

The expanded and acidic solution washed samples were drained from the final acidic solution, and each acid treated hydrogel sample was directly put into a 30 mm diameter cylindrical tube mould that should be longer than the length of gel and have only one end open. The swollen gel inside the mould was then put into a −20° C. freezer for 8-24 hours and then transferred into the freeze-dryer to produce a freeze-dried superporous hydrogel (freeze-dried SPH).

Plasticisation

Each sample of freeze dried superporous hydrogel was plasticised using the following method. A 0.4 L lidded container with an inner surface that includes a moisture wicking material (for example, strips of moisture absorbent paper, moistened with 1 ml of water each). The container is heated to 60° C. for 5 minutes. A freeze-dried SPH sample was then put in the container (well away from the moisture wicking material) and the container replaced in the oven at 60° C. for 1 to 5 minutes (ideally 3 minutes) until the sample became malleable.

Compression

Each malleable (plasticised) freeze-dried SPH sample was carefully removed from the container and as shown in FIGS. 2A and 2B compressed along the hole (22) from the lateral side of the sample (20) with a rod (24) and folded along the compressed line as shown in FIGS. 2C and 2D and the resulting folded sample (30) of plasticised freeze dried super porous hydrogel was squeezed, as shown in FIG. 4A, into a cylindrical tube (36) with an I.D of 9~10 mm. This was achieved using a crimping machine that applies even radial compression along the long axis of the sample. The degree of swelling was measured by recording the weight of each sample of SPH material prior to swelling in distilled water at 37 C and recording the length and diameter of each swollen sample and noting the expansion % volume over time.

RESULTS As shown in Table 4 below, the SPH samples show an increase in % expansion as the pH of the acidic treatment solution increases from 1 to 12, with the greatest increase being recorded for the initial hydrogel samples treated with an acidic solution of from pH 1 to 3. Initial hydrogel samples treated with acidic solutions with a pH of 4 to 11 produce SPH samples which continue to increase in % expansion but the rate of this increase plateaus, and when a treatment solution of pH12 is used, the respective SPH sample disintegrates.

TABLE 4

| pH | Appearance | Shape | Expansion % wt |
|---|---|---|---|
| 1 | translucent | Defined cylinder | 16.8 |
| SGF (pH 1.3) | translucent | Defined cylinder | 17.0 |
| 2 | hazy | Defined cylinder | 22.6 |
| 3 | Slightly hazy | Slightly distorted cylinder | 30.2 |
| 4 | transparent | Distorted cylinder | 32.5 |
| 5 | transparent | Distorted cylinder | 33.9 |
| 6 | transparent | Distorted cylinder | 35.4 |
| 7 | transparent | Distorted cylinder | 28.7 |
| 8 | transparent | Distorted cylinder | 31.7 |
| 9 | transparent | Distorted cylinder | 32.8 |
| 10 | transparent | Very Distorted cylinder | 35.6 |
| 11 | transparent | Very Distorted cylinder | 42.5 |
| 12 | transparent | Amorphous | 90.1 |

Other key observations made during this experiment include: i) as the pH of the acidic solution used to treat the initial hydrogel is increased, the target SPH become less mechanically stable. This is observed by the loss of structural integrity in the SPH sample; the SPH sample has defined cylinder shape when an acidic treatment solution on pH 1 to 3 is used, but this shape becomes progressively more distorted as the pH increases to pH 11, and finally becomes amorphous when the treatment solution is at pH 12. ii) Although expansion increases as the pH of the acidic solution used as the soaking liquid increases, the target SPH material becomes progressively more unusable. iii) A desirable hazy/translucent appearance in the SPH is only observed when the initial hydrogel from which the respective SPH sample is formed is treated with an acidic solution with a pH of 1 to 3. It is understood that this haziness/translucence is caused by the porosity in the hydrogel.

The time needed to treat each sample with high humidity conditions was found to vary significantly, depending on the pH of the acidic solution.

CONCLUSION: The pH of the acidic solution used to treat the initial hydrogel material is particularly important for to ensure good processability and must be less than or equal to pH 3 to provide optimum conditions for the desired pore size and desired rate of expansion, whilst maintaining structural integrity.

Example 4: Experiment to Determine the Effect of pH and Treatment with Potassium Chloride on Swelling Behaviour The synthesis and polymerisation step used in Example 1 was used to prepare twenty (20) separate samples of initial hydrogel material, each individually cast in a mould (10). The samples of initial hydrogel material were then split into four (4) batches; one batch was treated with an acidic solution at pH 1, another treated with a solution at pH 1.3, another with a solution at pH 2 and the remaining treated with a solution at pH 7. The five samples in each batch were then treated with an aqueous solution containing from 0M to 1M of potassium chloride salt. Following this, each of the samples were freeze dried, plasticised and compressed, as described above in Example 3, and the resulting shaped SPH samples were immersed in distilled water at 37 C and recording the length mm and diameter mm of each swollen sample and noting the expansion % volume over time.

The complete experiment was repeated 4 times and each % volume increase value presented in Table 5 below, is an average of the four results obtained for the corresponding samples from each repeat of the experiment. The results show that the concentration of potassium chloride has very little effect on the final swelling weight on soaking, in the case of samples produced from initial hydrogel samples that are treated with an acidic solution with a pH of 1 to 2, although as expected from Experiment 3 above, a much larger % weight increase is observed when the treatment solution is at pH 7. However, very surprisingly, it is found that the % volume change after 60 minutes is effected by the concentration of potassium chloride; specifically, the % volume expansion increases as the concentration of potassium chloride increases from 0M to around 0.134M (10 g), and then the expansion decreases when the concentration reaches around 0.5M.

CONCLUSION: >0 to 0.134M addition of KCl is a particularly useful range.

TABLE 5

| pH of Acidic treatment solution | Amount of KCl in the salt treatment solution | % volume increase after 10 mins (Results are an average of 4 repeats) | % volume increase after 60 mins (Results are an average of 4 repeats) | Wt % |
|---|---|---|---|---|
| pH1 | 0 | 200 | 265 | 23.4 |
| | 0.067M | 188 | 318 | 22.9 |
| | 0.134M | 233 | 361 | 24.7 |
| | 0.5M | 132 | 285 | 26.1 |
| | 1M | 231 | 323 | 27.9 |
| pH 1.3 | 0 | 216 | 337 | 23.8 |
| | 0.067M | 162 | 352 | 24.0 |
| | 0.134M | 92 | 318 | 23.6 |
| | 0.5M | 78 | 368 | 25.2 |
| | 1M | 65 | 156 | 24.5 |
| pH2 | 0 | 74 | 173 | 28.2 |
| | 0.067M | 64 | 227 | 26.1 |
| | 0.134M | 56 | 164 | 24.7 |
| | 0.5M | 47 | 111 | 23.5 |
| | 1M | | | 41.4 |
| pH7 | 0 | 269 | 126 | 40.4 |
| | 0.067Mg | 110 | 379 | 41.1 |
| | 0.134M | 119 | 338 | 44.8 |
| | 0.5M | 100 | 180 | 40.2 |
| | 1M | 106 | 198 | 44.3 |
| sgf | | 105 | 214 | 24.1 |

Example 5: Experiment to Determine the Effect of Monovalent Metal Salt Concentration on the Processability of the Target SPH Material An important property of the required plasticised superporous hydrogel material is the ease with which it undergoes shaping, for example by folding/rolling/compressing, to enable it to be inserted it into a dosage capsule shell within a reasonable time frame, (desirably more than 1 minute but less than 60 minutes) and there is a fine balance between an SPH material that has excellent workability characteristics, and one which has become too soft. The present work has surprisingly established that for a given degree of water vapour treatment (exposure to moisture: % humidity and duration) used to plasticise an SPH sample, the "workability" (ease of folding/rolling/compressing) of the SPH sample increases as the KCl concentration increases, the SPH material become more 'workable'. However, too much KCl, typically when the metal salt concentration is above 0.15M, the target SPH becomes too soft to be worked easily.

A useful outcome of this observation is that the addition of KCl assists to control and optimise the amount of moisture exposure (duration and/or % humidity) a sample of dried SPH material needs to soften it, with concentrations of KCl salt >0M up to 0.15 M enabling a reduction in humidity/shortening the time of moisture exposure, compared with the case when no KCl salt is used.

CONCLUSION: Optimal moisture exposure is obtained when a >0M to 0.15M monovalent salt solution is used.

The invention claimed is:

1. A process for preparing a plasticised superporous hydrogel comprising the steps:
   a) forming an initial hydrogel material in the absence of any blowing agent or other foaming means, wherein the initial hydrogel material comprises one or more selected from interpenetrating network structure, a semi-interpenetrating network structure and a simple cross-linked structure formed by providing a mixture comprising acrylamide and alginate and subjecting the mixture to polymerisation and/or cross-linking conditions;
   b) recovering the resulting initial hydrogel material formed in step a) and treating it with an acidic solution comprising one or more acids, and with a pH of ≤3;
   c) treating the initial hydrogel material formed in step a), either concurrently with, or after, treatment step b), with a ≥0M to ≤0.5M solution comprising one or more monovalent metal salts;
   d) drying the resulting initial hydrogel material formed in step c) using freeze drying, to produce a dried superporous hydrogel material;
   e) treating the resulting dried superporous hydrogel material to plasticise its structure; and
   f) recovering the resulting plasticised superporous hydrogel material.

2. The process according to claim 1 wherein the resulting plasticised superporous hydrogel material is in the form of an individually separate sample comprising a body that has an internal structure comprising plasticised superporous hydrogel material and an outer surface, wherein each sample comprises one or more through-holes which form a passageway that extends within the internal structure of the body and between a first opening in a first portion of the outer surface of the hydrogel material body and a second opening in a second portion of the outer surface of the hydrogel material body.

3. The process according to claim 1, wherein individual samples of the initial hydrogel material are prepared by filling suitable moulds with a reaction mixture comprising acrylamide and alginate, prior to subjecting the mixture to polymerisation and/or cross-linking conditions, and demoulding the resulting individual samples of the initial hydrogel material.

4. The process according to claim 3, wherein the individual samples of the initial hydrogel material are cube-, cuboid-, ovoid-, pellet-, bead-, ball-, cylinder-, rod- or irregularly-shaped.

5. The process according to claim 1 wherein step e) includes subjecting the superporous hydrogel to >50% humidity conditions.

6. The process according to claim 1 wherein the one or more monovalent metal salts is a water-soluble alkali metal salt.

7. The process according to claim 1 wherein the one or more acids are selected from an inorganic acid and/or an organic acid.

8. The process according to claim 1 wherein the acidic solution comprises one or more selected from gastric fluid and simulated gastric fluid.

9. The process according to claim 1 further comprising the step of applying a compressive force to the resulting plasticised superporous hydrogel material to reduce the volume of at least some of the pores therein.

10. The process according to claim 1 comprising a further step of inserting the resulting plasticised superporous hydrogel material into a capsule dosage formulation shell to produce a capsule dosage formulation.

11. The process according to claim 10 wherein the resulting plasticised superporous hydrogel material is inserted into the capsule dosage formulation shell using one or more techniques to reduce the overall size of the resulting hydrogel body prior to insertion into the capsule dosage formulation shell, selected from: the exertion of pressure, folding, extrusion, and the application of bi-and/or tri-lateral compression.

12. The process according to claim 11 wherein the resulting plasticised superporous hydrogel material is extruded through a hollow tapered tube prior to insertion into the capsule dosage formulation shell.

13. A method of forming a formulation suitable for oral administration comprising including one or more plasticised superporous hydrogels prepared by the process of claim 1.

14. The method according to claim 13 further comprising including one or more pharmaceuticals and/or nutraceuticals.

\* \* \* \* \*